US011110031B2

(12) United States Patent
Song et al.

(10) Patent No.: US 11,110,031 B2
(45) Date of Patent: Sep. 7, 2021

(54) AIR POCKET-TYPE MASSAGE DEVICE

(71) Applicant: CERAGEM CO., LTD., Chungcheongnam-do (KR)

(72) Inventors: Hanrim Song, Gyeonggi-do (KR); Keunyoung Paek, Chungcheongnam-do (KR); Changsu Park, Gyeonggido (KR); Sangho Choi, Chungcheongnam-do (KR)

(73) Assignee: CERAGEM CO., LTD., Chungcheongnam-do (KR)

( * ) Notice: Subject to any disclaimer, the term of this patent is extended or adjusted under 35 U.S.C. 154(b) by 242 days.

(21) Appl. No.: 15/539,513

(22) PCT Filed: Nov. 16, 2015

(86) PCT No.: PCT/KR2015/012293
§ 371 (c)(1),
(2) Date: Jun. 23, 2017

(87) PCT Pub. No.: WO2016/104951
PCT Pub. Date: Jun. 30, 2016

(65) Prior Publication Data
US 2017/0348189 A1   Dec. 7, 2017

(30) Foreign Application Priority Data

Dec. 24, 2014 (KR) .................. 10-2014-0188346

(51) Int. Cl.
*A61H 23/00* (2006.01)
*A61G 7/05* (2006.01)
(Continued)

(52) U.S. Cl.
CPC .............. *A61H 23/04* (2013.01); *A61F 7/00* (2013.01); *A61F 7/0085* (2013.01); *A61F 7/02* (2013.01);
(Continued)

(58) Field of Classification Search
CPC ........ A61H 23/04; A61H 9/0078; A61H 9/00; A61G 7/05; A61G 7/05776; A61F 7/0085;
(Continued)

(56) References Cited

U.S. PATENT DOCUMENTS 5,718,369 A     2/1998  Delisle et al.
5,762,618 A *   6/1998  Yamanaka ............... A47C 4/54
                                                601/148

(Continued)

FOREIGN PATENT DOCUMENTS

CN      2719116 Y    8/2005
CN       174962      6/2006
(Continued)

OTHER PUBLICATIONS

International Search Report Issued in Corresponding PCT Application No. PCT/KR2015/012293, dated Feb. 11, 2016.
(Continued)

*Primary Examiner* — Tu A Vo
(74) *Attorney, Agent, or Firm* — Norton Rose Fulbright US LLP

(57) ABSTRACT

An air pocket-type massage device is provided. The device can include: a bed unit (100) which is for supporting parts of the body of a user; a massage module (200) which is disposed on the bed unit (100) and includes a plurality of air pockets; and a position adjuster (300) which is provided on the bed unit (100) and enables changing of the position of the massage module (200).

5 Claims, 4 Drawing Sheets

(51) Int. Cl.
    *A61H 9/00*     (2006.01)
    *A61F 7/02*     (2006.01)
    *A61H 23/04*     (2006.01)
    *A61F 7/00*     (2006.01)
    *A61G 7/057*     (2006.01)

(52) U.S. Cl.
    CPC ................ *A61G 7/05* (2013.01); *A61H 9/00* (2013.01); *A61H 9/0078* (2013.01); *A61F 2007/0043* (2013.01); *A61F 2007/0055* (2013.01); *A61F 2007/0071* (2013.01); *A61F 2007/0091* (2013.01); *A61F 2007/0222* (2013.01); *A61F 2007/0268* (2013.01); *A61G 7/05776* (2013.01); *A61H 2201/0103* (2013.01); *A61H 2201/0142* (2013.01); *A61H 2201/0207* (2013.01); *A61H 2201/1238* (2013.01); *A61H 2205/106* (2013.01)

(58) Field of Classification Search
    CPC ...... A61F 7/02; A61F 7/00; A61F 2007/0091; A61F 2007/0071; A61F 2007/0268; A61F 2007/0043; A61F 2007/0055
    See application file for complete search history.

(56) References Cited

U.S. PATENT DOCUMENTS

| | | | | | |
|---|---|---|---|---|---|
| 6,848,137 | B1* | 2/2005 | Barnes | ................ | A47C 20/048 |
| | | | | | 5/615 |
| 6,984,197 | B2* | 1/2006 | Sugiyama | ............ | A61H 1/0266 |
| | | | | | 482/148 |
| 7,195,604 | B2* | 3/2007 | Nakamura | ............. | A61H 23/04 |
| | | | | | 601/136 |
| 7,549,966 | B2* | 6/2009 | Fujii | .................... | A61H 9/0078 |
| | | | | | 601/133 |
| 9,259,098 | B2* | 2/2016 | Williams | ............. | A47C 27/088 |
| 2003/0096685 | A1 | 5/2003 | Weitzman | | |
| 2006/0142676 | A1* | 6/2006 | Fujii | .................. | A61H 15/0078 |
| | | | | | 601/98 |
| 2006/0217643 | A1* | 9/2006 | Yonekawa | ........... | A61H 9/0078 |
| | | | | | 601/148 |
| 2007/0016119 | A1* | 1/2007 | Inada | .................... | A61H 9/0078 |
| | | | | | 601/151 |
| 2009/0099489 | A1* | 4/2009 | Tanizawa | ............. | A61H 9/0078 |
| | | | | | 601/84 |
| 2010/0198120 | A1* | 8/2010 | Tago | .................... | A61H 1/0237 |
| | | | | | 601/134 |
| 2010/0198121 | A1* | 8/2010 | Tago | .................... | A61H 9/0078 |
| | | | | | 601/150 |
| 2010/0318004 | A1* | 12/2010 | Numata | ................. | A61H 7/007 |
| | | | | | 601/16 |
| 2011/0125070 | A1* | 5/2011 | Lu | ........................ | A61H 1/0292 |
| | | | | | 601/115 |
| 2013/0000041 | A1* | 1/2013 | Receveur | ............... | A61G 7/015 |
| | | | | | 5/618 |
| 2013/0226051 | A1* | 8/2013 | Lu | ........................ | A61H 7/007 |
| | | | | | 601/99 |
| 2015/0157521 | A1* | 6/2015 | Williams | ............. | A47C 27/088 |
| | | | | | 5/81.1 R |
| 2015/0290061 | A1* | 10/2015 | Stafford | ............. | A63B 22/0089 |
| | | | | | 5/600 |

FOREIGN PATENT DOCUMENTS

| | | |
|---|---|---|
| CN | 201977279 | 9/2011 |
| CN | 202950322 U | 5/2013 |
| CN | 203028687 | 7/2013 |
| CN | 203075169 | 7/2013 |
| CN | 203328320 U | 12/2013 |
| CN | 203591406 | 5/2014 |
| EP | 1629819 | 3/2006 |
| JP | 09192184 | 7/1997 |
| JP | H1057436 A | 3/1998 |
| JP | H10118143 | 5/1998 |
| JP | 2001340407 | 12/2001 |
| JP | 2002369847 A | 12/2002 |
| JP | 2003335323 A | 11/2003 |
| JP | 2004344589 | 12/2004 |
| JP | 3783793 | 6/2006 |
| JP | 2006192314 | 7/2006 |
| JP | 2008245823 | 10/2008 |
| JP | 2010-148561 | 7/2010 |
| JP | 2013-106833 | 6/2013 |
| JP | 2014124514 A | 7/2014 |
| KR | 200362350 | 9/2004 |
| KR | 20060010815 | 2/2006 |
| KR | 100804733 | 2/2008 |
| KR | 101288410 | 7/2013 |
| KR | 101383252 | 4/2014 |
| RU | 2068683 | 8/1996 |
| WO | WO 2012/114796 | 8/2012 |

OTHER PUBLICATIONS

Office Action Issued in Corresponding European Patent Application No. 15873479.8, dated Dec. 17, 2019.

Office Action from the Japanese Patent Office issued in corresponding Japanese Patent Application No. 2019-078422 dated May 26, 2020.

* cited by examiner

AIR POCKET-TYPE MASSAGE DEVICE

TECHNICAL FIELD

Cross-Reference to Related Applications

This application is a national phase application under 35 U.S.C. § 371 of International Application No. PCT/KR2015/012293, filed Nov. 16, 2015, which claims priority to Korean Patent Application No. 10-2014-0188346, filed Dec. 24, 2014. The contents of the referenced applications are incorporated into the present application by reference.

The present invention relates to an air pocket-type massage device capable of changing a position of a massage module using a position adjusting means according to a change in stature of a user when a part of the body, particularly, the calves, of the user are massaged.

BACKGROUND ART

As a conventional massage device, Korean Patent Registration No. 10-1288410 (Jul. 16, 2013, hereinafter, referred to as prior art) discloses "Auto heat massage chair for preventing of varicose veins and calf diet".

The prior art is configured to include an airbag that is sealed, contractible, and expandable and provided on one side of the auto heat massage chair, a sheet heating element provided on one side surface portion of the airbag to be in surface-contact with the one side surface of the airbag, and heating air inside the sealed airbag by heating the whole of the one side surface in surface-contact with the airbag to expand the airbag; and a pressurizer provided on the other side surface portion of the sheet heating element not to be in contact with the airbag and pressurizing the sheet heating element.

According to the prior art, airbag-pressure massage and thermal treatment effects may be obtained only using a simple configuration without additional elements such as an air compressor and a heater by heating air inside the sealed airbag to expand the airbag and providing the thermal treatment effect using the heated air.

Also, the prior art is configured to include a supporter for mounting calves or feet thereon and airbags at the supporters to perform a massage operation.

However, in the prior art, since the supporters always remain in a protruded state, a volume of the device is large and it is not easy to store and handle the device and an external aesthetic of the device is not good.

Also, since each user has a different stature, a length of calves may be different. Accordingly, since acupressure points of a user of tall stature and a user of short stature may be different, when positions of the airbags are fixed, like in the prior art, it is impossible to position the airbags at precise acupressure points, thereby reducing a massage effect as well as decreasing user satisfaction.

SUMMARY OF THE INVENTION

It is an aspect of the present invention to flexibly correspond to a change in stature of a user by changing a position of a massage module using a position adjusting means according to the change in the stature of the user when parts of the body, particularly, the calves, of the user are massaged.

It is another aspect of the present invention to maximize massage effects by gathering the legs of the user not to deviate from each other during a massage operation by making contact points between air pockets and the calves of the user different using air pockets with different widths in the massage module.

It is still another aspect of the present invention to accommodate deformation between expansion and contraction of the air pockets using a flexible sheath which the air pockets are built into so that a volume of a massage device is reduced and storage or handling of the massage device is facilitated.

According to one aspect of the present invention, an air pocket-type massage device includes a bed portion that supports a part of a body of a user, a massage module disposed on the bed portion and including a plurality of air pockets, and a position adjusting means provided at the bed portion to change a position of the massage module.

A transfer module may include a transfer plate on which the air pockets of the massage module are mounted, a guide provided at the bed portion, and a transfer portion provided at the transfer plate to move along the guide.

The massage module may include a plurality of narrow first air pockets disposed at an inner side and a plurality of wide second air pockets corresponding to the first air pockets and disposed at an outer side.

The massage module may further include a flexible sheath, which the air pockets are built into, configured to be stretchable according to an operation of the air pockets.

A wrinkled portion may be further provided on one side of the flexible sheath.

According to embodiments of the present invention, an air pocket-type massage device can increase user convenience by removing an inconvenience caused by a difference in statures of users by flexibly corresponding to a change in stature of a user by changing a position of a massage module using a position adjusting means according to the change in stature of the user when parts of the body, particularly, the calves, of the user are massaged.

According to embodiments of the present invention, massage effects can be maximized by gathering the legs of the user not to deviate from each other during a massage operation by making contact points between air pockets and the calves of the user different using air pockets with different widths in the massage module.

According to embodiments of the present invention, since it is possible to change the position of the massage module according to a difference in statures of users, an optimal arrangement structure can be configured using a minimal quantity of air pockets without considering differences in statures of users such that not only the quantity of air pockets can be reduced but also costs thereof can be reduced.

According to embodiments of the present invention, deformation between expansion and contraction of the air pockets can be accommodated by using a flexible sheath which the air pockets are built into so that a volume of a massage device is reduced and storage or handling of the massage device is facilitated.

According to embodiments of the present invention, since a massage operation is performed on a plane, a user may sit or lie in a comfortable position, and accordingly an efficient massage effect can be obtained.

DETAILED DESCRIPTION OF THE INVENTION

An air pocket-type massage device according to one embodiment of the present invention will be described with reference to the attached drawings.

As shown in FIGS. 1 to 4, the air pocket-type massage device according to one embodiment of the present invention includes a bed portion 100, a massage module 200 including a plurality of air pockets 210 and 220, and a position adjusting means 300 that allows transfer of the massage module 200.

Figure 1:
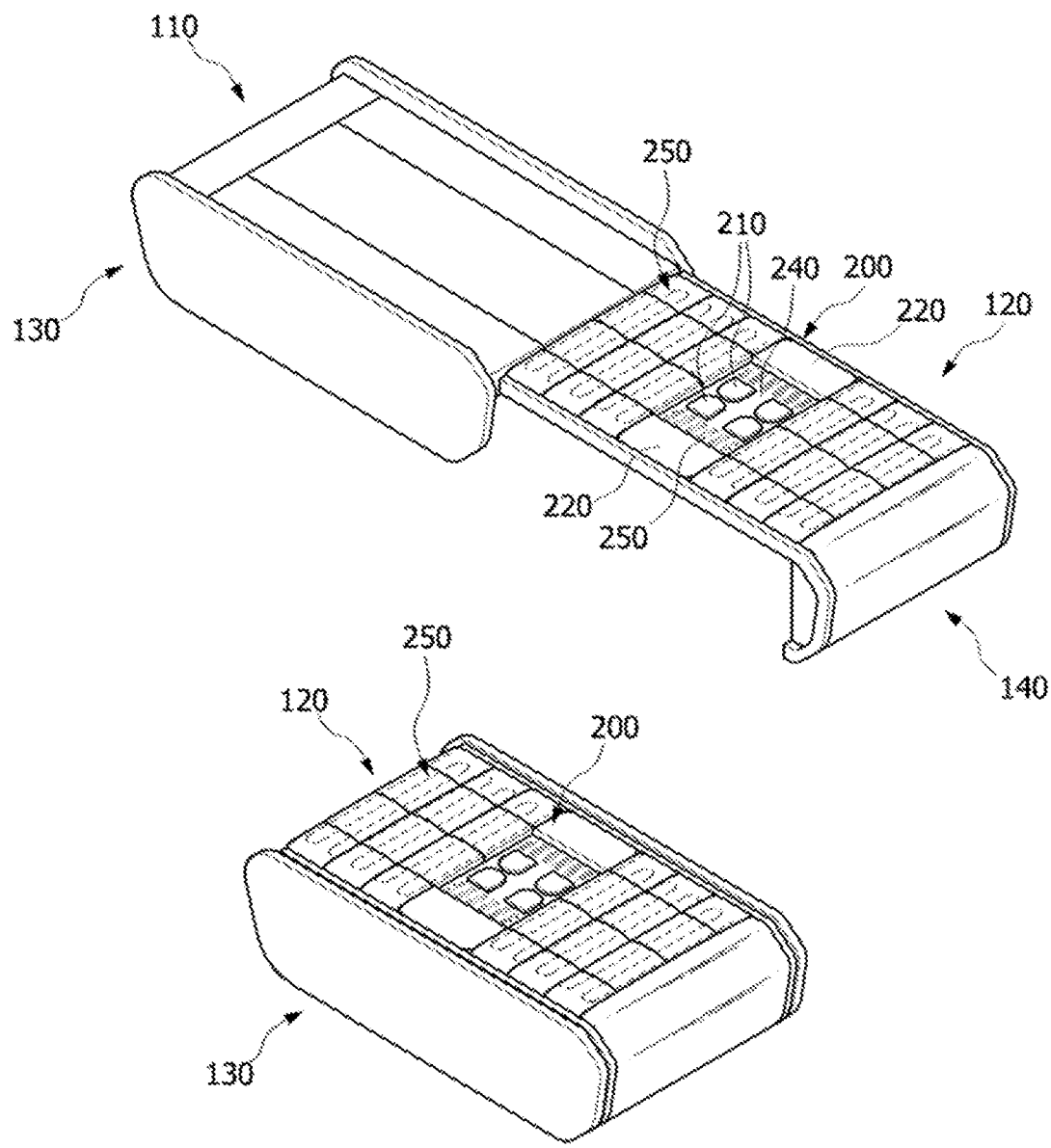
FIG. 1 is a perspective view of an air pocket-type massage device according to one embodiment of the present invention.

First, as shown in FIG. 1, the bed portion 100 is configured to allow a user to lie or sit thereon and supports the upper body or lower body of the user.

For this, the bed portion may be manufactured in various shapes, and for example, may be horizontally disposed in a bed or mattress shape or may include a back, a seat, and a leg supporter disposed below the seat, like a chair.

In the present invention, as shown in FIG. 1, the bed portion 100 configured to have a bed or mattress shape and include a first bed portion 110 that supports the upper body of the user with both sides to which supporting members 130 are connected and a second bed portion 120 that supports the lower body of the user will be described as an example.

In this case, for convenience of use or handling, the bed portion 100 may be configured in a shape in which the first bed portion 110 and the first bed portion 110 are folded or may be configured to allow the second bed portion 120 to slide from the first bed portion 110 and be unfolded or folded as shown in FIG. 1.

Here, when the bed portion is configured as a sliding type, a support 140 may be provided at the second bed portion 110 and an automatic sliding module may be provided at the support 140 to be automatically driven or directly unfolded or folded by the user with hands as necessary.

Accordingly, when the bed portion according to one embodiment of the present invention is unfolded, since the upper body of the user is positioned at the first bed portion 110 and the lower body, particularly, the calves, of the user are positioned at the second bed portion 120, a massage operation is performed on a horizontal plane.

Figure 2:
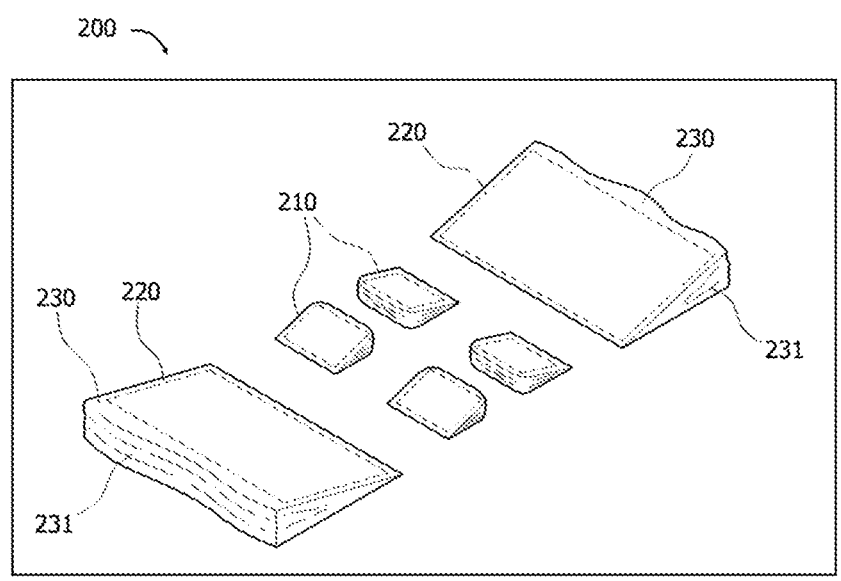
FIG. 2 is an enlarged perspective view of a massage module configured as an air pocket according to one embodiment of the present invention.
Figure 3:
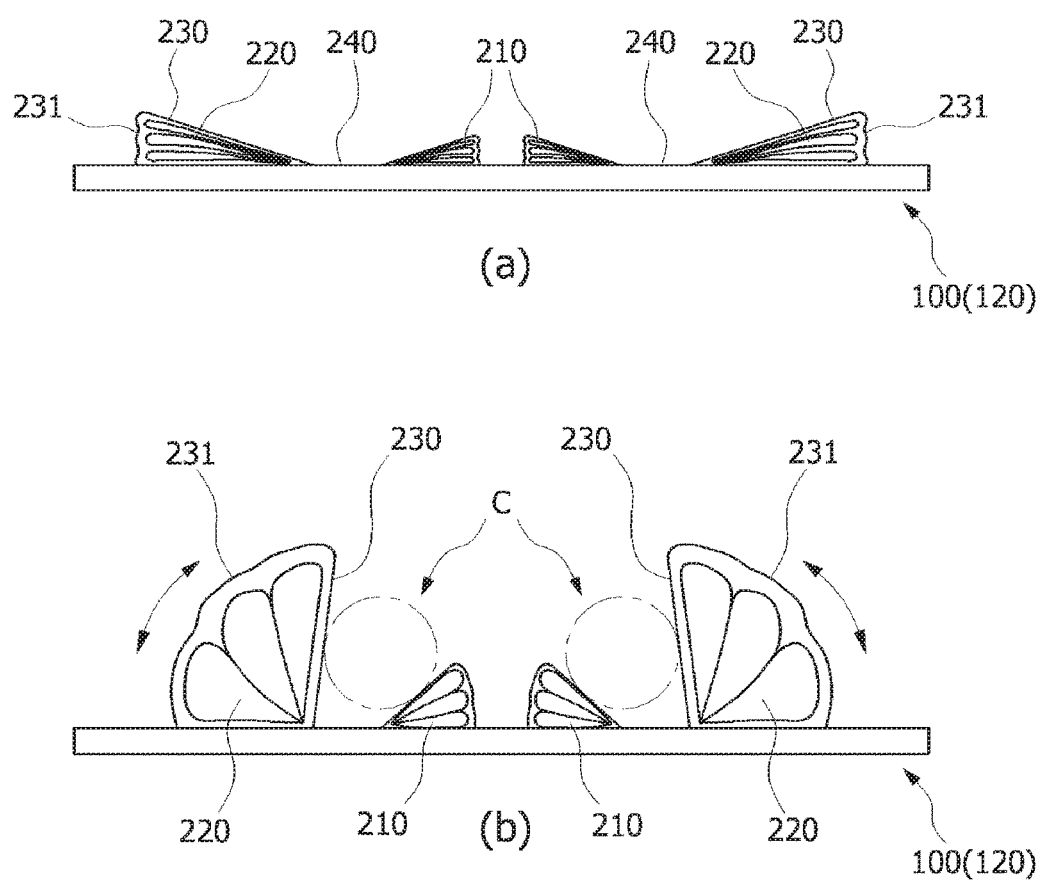
FIG. 3 is a cross-sectional view illustrating an operational state of the massage module according to one embodiment of the present invention.

Next, as shown in FIGS. 1 to 3, the massage module 200 according to one embodiment of the present invention includes the plurality of air pockets 210 and performs the massage operation by contracting and expanding the air pockets 210.

First, the massage module 200 according to one embodiment of the present invention includes an air compressor (not shown) for injecting air into each of the air pockets 210, and the air compressor is connected to each of the air pockets 210 through an injection tube.

The air pockets according to one embodiment of the present invention massage the lower body, particularly, the calves of the user.

In this case, in a conventional air pocket-type massage device, when an air pocket is expanded, the air pocket and a part in contact with the calf of the user are positioned at the same level. Accordingly, the legs of the user may be spread during the massage operation.

Accordingly, in the present invention, the legs of the user may be collected not to be spread during the massage operation as describe above by improving a size and an arrangement structure of the air pockets as follows.

For this, the air pockets of the massage module 200 include narrow first air pockets 210 disposed at an inner side and wide second air pockets 220 disposed at an outer side corresponding to the first air pockets 210.

First, widths of the first and second air pockets 210 and 220 refer to approximately lateral lengths when the air pockets are viewed from the front as shown in FIG. 3.

Accordingly, the width of the first air pocket 210 is formed to be smaller than that of the second air pocket 220.

When air is supplied to the air pockets and the air pockets are expanded as shown in FIG. 3, the first air pockets 210 disposed at the inner side come into contact with internal lower points of the calves of the user and the second air pockets 220 come into contact with external upper points of the calves of the user.

That is, since the first air pockets 210 apply forces to the calves upwards from the inner side at the same time that the second air pockets 220 apply forces to the calves downwards from the outer side, the legs of the user are naturally collected inward by the pressures by the second air pockets 220.

When the air pockets 210 and 220 are expanded and generate the same pressure, the first air pockets 210 support the lower points of the calves as levers, and in this state, the second air pockets 220 apply pressure toward the tops of the calves. Accordingly, the overall force is applied inwards.

As a result, when the air pockets according to one embodiment of the present invention massages the legs of the user while the acupressure points of the first and second air pockets 210 and 220 are different, not only are the legs of the user prevented from being spread but massage effects may also be increased.

Also, in the massage module 200 according to one embodiment of the present invention, since the first air pockets 210 and the second air pockets 220 have different widths, a difference in acupressure areas is generated. Accordingly, the plurality of first air pockets 210 having a relatively narrow width are provided to have acupressure areas corresponding to those of the second air pockets 220.

In addition, the air pockets of the massage module 200 according to one embodiment of the present invention are disposed above a transfer plate 310, which will be described below, and a mounting portion 240 on which the calves are placed is disposed between the first and second air pockets 210 and 220.

In this case, the air pockets 210 and 220 are built into a flexible sheath 230 connected to one side of the transfer plate 310.

Wrinkled portions 231 are connected to an outer side of the flexible sheath 230. The wrinkled portions 231 accommodate operations of the air pockets 210 and 220 through stretchability when the air pockets 210 and 220 are contracted and expanded.

The wrinkled portions 231 may be preferably formed of a material having an elastic force such as rubber, spandex, and the like to have stretchability.

When the air pockets 210 and 220 are contracted as shown in FIG. 3(a), the wrinkled portions 231 of the flexible sheath 230 remains in a contracted state. When the air pockets 210 and 220 are contracted as shown in FIG. 3(b), the wrinkled portions 231 of the flexible sheath 230 are elongated. Here, the calves of the user positioned at the mounting portion 240 are pressurized and a process in which the wrinkled portions 231 are contacted with a contraction of the air pockets 210 and 220 is repeated again to perform the massage process.

In addition, as shown in FIG. 1, the second bed portion 120 according to one embodiment of the present invention includes a heating portion 250 and supplies heat to the legs of the user to additionally provide a heat treatment effect during massage to further increase a massage effect.

Accordingly, the heating portion 250 includes heating wires that are arranged in the whole second bed portion 120 and may be divided into heating wires disposed above and below the mounting portion 240 between the air pockets 210 and 220 and a heating wire disposed on the mounting portion 240.

In this case, the heating wires of the heating portion 250 may be separately or simultaneously controlled. For example, the heating wires positioned above and below the mounting portion 240 may be simultaneously operated and only the heating wire disposed on the mounting portion 240 may be independently operated. Otherwise, all of the heating wires may be simultaneously operated and each of the heating wires disposed on each part may be controlled to be independently operated as necessary.

Furthermore, the heating portion may include a lamp, a plate-shaped heating body, or the like, which are not shown in the drawing, disposed in addition to the above-described heating wires to perform the same function.

Figure 4:
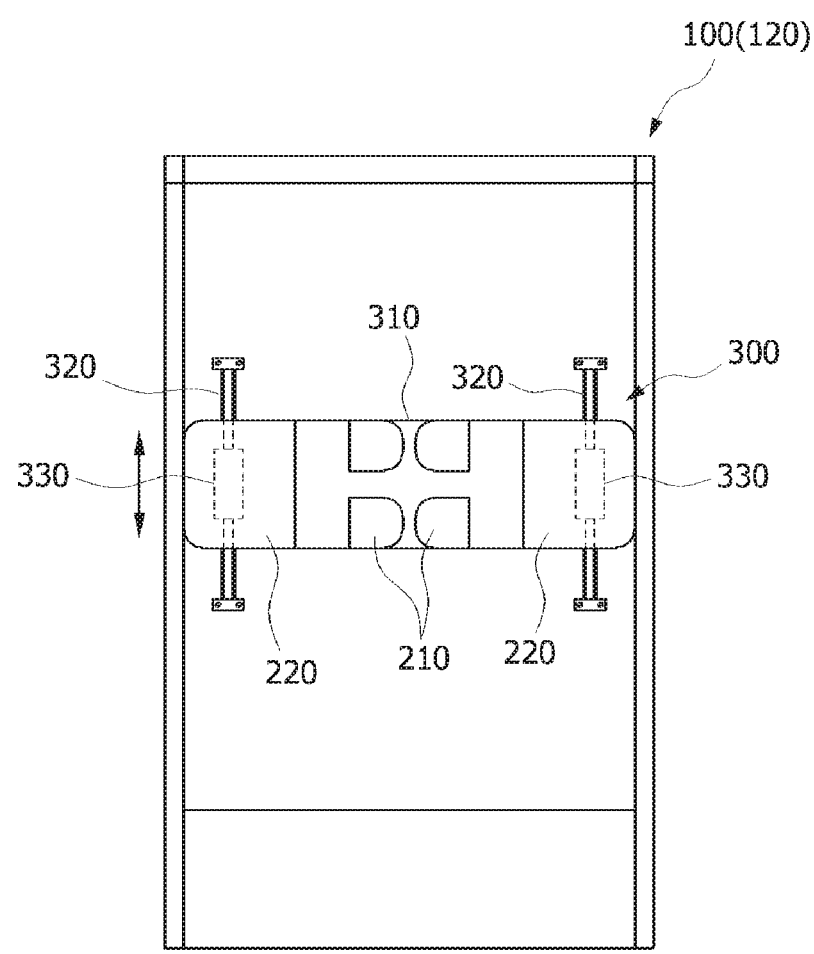
FIG. 4 is a plane view of a position adjusting means according to one embodiment of the present invention.

Meanwhile, as shown in FIG. 4, the position adjusting means 300 may change the position of the massage module 200 to provide convenience of the massage operation.

Generally, males and females who are users have a difference in statures, and there is a difference in statures of people of the same gender.

In this case, when a user lies on the bed portion, there is a large difference in positions of calves C depending on users. Here, when the position of the massage module 200 is fixed, the user has an inconvenience of having to position his or herself to place his or her calves C on the massage module 200 during the massage operation.

When a size of the bed portion is limited, a tall user's head may be deviate from the bed portion or be positioned at a corner to double the inconvenience.

When the position of the massage module 200 is fixed and the air pockets are arranged based on tall users to allow both tall users and short users to use the massage module 200, in consideration of a difference in statures of the users, the short users partially use the air pockets, and costs may be increased due to unnecessarily installed air pockets.

Conversely, in a case in which the number of air pockets is reduced based on the short users, when tall users use the massage module 200, the calves C of the users partially receive acupressure in such a way that it is impossible to increase massage effects, and satisfaction in the device may be decreased.

Accordingly, in the present invention, to solve the problems, the position adjusting means 300 capable of changing and adjusting the position of the massage module 200 is provided.

The position adjusting means 300 according the present invention includes the transfer plate 310 on which the air pockets 210 and 220 of the massage module 200 are mounted, a guide 320 provided at the bed portion, and transfer portion 330 provided at the transfer plate 310 to move along the guide 320.

First, the transfer plate 310 of the position adjusting means 300 is disposed above the bed portion, and in more detail, the second bed portion 120 and the first and second air pockets 210 and 220 are mounted on a top surface thereof.

In addition, the guide 320 of the position adjusting means 300 is mounted on the top surface of the second bed portion 120 as one pair of rails, and the transfer portion 330 of the position adjusting means 300 is mounted below the transfer plate 310 and disposed above the guide 320.

In this case, the transfer portion 330 may not only be a driving body with various shapes such as a roller, an LM guide, a geared motor, a ball screw, and the like but also a manual type through which a user may change the position of the massage module 200 or an automatic type through which the position of the massage module 200 may be changed by operating a remote control or a controller mounted on the massage device.

According to the position adjusting means 300 configured as described above, since the position of the massage module 200 is changed according to a stature of a user to allow the massage module 200 to move to a precise position of an acupressure point which is different for each user, massage effects as well as convenience of the user may be increased, and also a customized massage operation is possible.

Also, since an adequate number of air pockets may be disposed regardless to a difference in statures of users, the number of air pockets may be reduced, and accordingly costs thereof may be reduced.

With respect to this, as shown in FIGS. 2 and 3, organizing two narrow first air pockets 210 as a group for one wide second air pocket 220 is an appropriate arrangement structure for increasing massage effects while reducing a quantity of air pockets. However, as necessary, the arrangement structure of air pockets may be changed or the quantity thereof may be increased or decreased.

Unlike an existing massage device, the above-described air pocket-type massage device may accommodate and support the lower body of a user without an additional structure to improve external aesthetics.

Also, since it is unnecessary to install an additional structure, manufacturing costs may be reduced, the massage device may be configured to have a compact structure, and convenience of storing or handling the massage device may also be increased.

To control the air pocket-type massage device according to one embodiment of the present invention, the massage module disposed on the first bed portion is controlled by a controller, and a sub controller is provided at an automatic sliding module provided at the support of the second bed portion.

In this case, the sub controller controls and adjusts the automatic sliding module, the air compressor, the position adjusting means, the heating portion, and the like.

Although the air pocket-type massage device according to one embodiment of the present invention has been mainly described above with particular shapes and directions with reference to the attached drawings, it should be understood that various modification and changes of the present invention may be made by one of ordinary skill in the art and that the modifications and changes are included in the scope of the present invention.

DESCRIPTION OF REFERENCE NUMERALS

C: Calves
100: Bed portion

-continued

| | |
|---|---|
| 120: | Second bed portion |
| 110: | First bed portion |
| 130: | Supporting member |
| 140: | Support |
| 200: | Massage module |
| 210: | First air pockets |
| 220: | Second air pockets |
| 230: | Flexible sheath |
| 231: | Wrinkled portion |
| 240: | Mounting portion |
| 250: | Heating portion |
| 300: | Position adjusting means |
| 310: | Transfer plate |
| 320: | Guide |
| 330: | Transfer portion |

The invention claimed is:

1. A massage device comprising:

a first bed portion comprising a top surface configured to directly support an upper body of a user;

a second bed portion configured to support a lower body of a user, wherein the second bed portion is configured to slide over the top surface of the first bed portion;

a massage module disposed on the second bed portion and comprising a flexible sheath that includes a plurality of air pockets; and a position adjuster comprising a transfer plate on which the plurality of air pockets are mounted and provided above the first and second bed portions, wherein the position adjuster is configured to change a position of the massage module, wherein the plurality of air pockets comprise at least:

a first pair of air pockets and a second pair of air pockets disposed at an inner side in the transfer plate; and a third air pocket and fourth air pocket each disposed at a first outer side and an opposite second outer side, respectively, in the transfer plate, wherein each of the third and fourth air pockets have a larger width when compared with each of the first pair of air pockets and second pair of air pockets, wherein when the first and second pair of air pockets are expanded, portions of the flexible sheath that include the first and second pair of air pockets are configured to come into contact with internal lower points of the calves of the user and to apply forces to the calves upwards from the inner side, and wherein when the third and fourth air pockets are expanded, portions of the flexible sheath that include the third and fourth air pockets are configured to come into contact with external upper side points of the calves of the user and to apply forces to the calves downwards from the outer side.

2. The massage device of claim 1, wherein the position adjuster further comprises a guide provided at the second bed portion, and a transfer portion provided at the transfer plate to move along the guide.

3. The massage device of claim 1, wherein a heating portion configured to supply heat is provided in a mounting portion disposed between the the third air pocket and the fourth air pocket.

4. The massage device of claim 1, wherein the flexible sheath is configured to be stretchable according to an operation of each of the at first pair of air pockets, second pair of air pockets, third air pocket and fourth air pocket.

5. The massage device of claim 1, wherein the flexible sheath comprises a wrinkled portion.

* * * * *

UNITED STATES PATENT AND TRADEMARK OFFICE
CERTIFICATE OF CORRECTION

| | | |
|---|---|---|
| PATENT NO. | : 11,110,031 B2 | Page 1 of 1 |
| APPLICATION NO. | : 15/539513 | |
| DATED | : September 7, 2021 | |
| INVENTOR(S) | : Song et al. | |

It is certified that error appears in the above-identified patent and that said Letters Patent is hereby corrected as shown below:

In the Claims

<u>Claim 3, Column 8, Line 25:</u>
Delete "between the the" and replace with -- between the --.

<u>Claim 4, Column 8, Line 29:</u>
Delete "the at first" and replace with -- the first --.

Signed and Sealed this
Fourteenth Day of December, 2021

Drew Hirshfeld
*Performing the Functions and Duties of the*
*Under Secretary of Commerce for Intellectual Property and*
*Director of the United States Patent and Trademark Office*